US008727971B2

(12) United States Patent
Takami et al.

(10) Patent No.: US 8,727,971 B2
(45) Date of Patent: May 20, 2014

(54) LIGHT-SOURCE DRIVER FOR PORTABLE ENDOSCOPE

(75) Inventors: Satoshi Takami, Saitama (JP); Kunikiyo Kaneko, Saitama (JP); Hiroto Watanabe, Tokyo (JP); Masahiko Sasaki, Chiba (JP); Eiji Tozawa, Saitama (JP)

(73) Assignee: Hoya Corporation, Tokyo (JP)

( * ) Notice: Subject to any disclaimer, the term of this patent is extended or adjusted under 35 U.S.C. 154(b) by 1393 days.

(21) Appl. No.: 11/960,831

(22) Filed: Dec. 20, 2007

(65) Prior Publication Data

US 2008/0262317 A1    Oct. 23, 2008

(30) Foreign Application Priority Data

Dec. 20, 2006  (JP) .................................. 2006-342152

(51) Int. Cl.
*A61B 1/06* (2006.01)
(52) U.S. Cl.
USPC .......................................... 600/178; 600/179
(58) Field of Classification Search
USPC .................... 600/178, 179; 362/574
See application file for complete search history.

(56) References Cited

U.S. PATENT DOCUMENTS

| 6,033,360 | A * | 3/2000 | Sano et al. ..................... 600/178 |
| 6,135,947 | A * | 10/2000 | Watanabe et al. ............. 600/178 |
| 6,307,332 | B1 * | 10/2001 | Noguchi et al. ............. 315/362 |
| 6,368,270 | B1 | 4/2002 | Takami |
| 6,494,827 | B1 * | 12/2002 | Matsumoto et al. .......... 600/118 |
| 7,001,331 | B2 * | 2/2006 | Kaji .............................. 600/132 |
| 2002/0137987 | A1 * | 9/2002 | Watanabe et al. ............. 600/178 |
| 2005/0033119 | A1 * | 2/2005 | Okawa et al. ................. 600/249 |
| 2007/0038030 | A1 | 2/2007 | Kaneko et al. |
| 2007/0039077 | A1 | 2/2007 | Takami |
| 2009/0187077 | A1 * | 7/2009 | Hosoda et al. ................ 600/178 |

FOREIGN PATENT DOCUMENTS

| JP | 9-98946 | 4/1997 |
| JP | 09122072 A * | 5/1997 ............... A61B 1/06 |
| JP | 2002-209845 | 7/2002 |
| JP | 2003-319906 | 11/2003 |
| JP | 2006-305338 | 11/2006 |

OTHER PUBLICATIONS

English language Abstract of JP 2003-319906.
U.S. Appl. No. 11/960,879 to Takami et al., which was filed on Dec. 20, 2007.
Japan Office action, dated Dec. 13, 2011 along with an english translation thereof.

* cited by examiner

*Primary Examiner* — Philip R Smith
*Assistant Examiner* — Rynae Boler
(74) *Attorney, Agent, or Firm* — Greenblum & Bernstein, P.L.C.

(57) ABSTRACT

A light-source driver for a light-source, detachable from an endoscope body includes a first switch, a pilot lamp, a warning lamp, a second switch, and a light switcher. The first switch switches between the On-state and Off-state in connection with the attachment and detachment of the light-source to the endoscope body. The pilot lamp indicates that the illumination light source is energized. The warning lamp indicates that the output voltage of a battery has dropped below a predetermined value. The second switch switches the warning lamp between the On-state and Off-state in connection with the On-state and Off-state of the first switch. The light switcher switches the pilot lamp to the Off-state and enables the second switch when the second switch is set to the On-state and the output voltage has declined to or below the predetermined value.

20 Claims, 3 Drawing Sheets

LIGHT-SOURCE DRIVER FOR PORTABLE ENDOSCOPE

BACKGROUND OF THE INVENTION

1. Field of the Invention

The present invention relates to a light-source driver applied to a battery-powered light-source unit for a portable endoscope where the light-source unit is detachable from the body of the endoscope.

2. Description of the Related Art

In general, a light-source unit is configured to be detachable from a portable endoscope. A battery is generally used as an electric power source of the light-source unit and a main switch for lighting the light source is provided on the body of the light-source unit. In mounting the light-source unit on the body of the endoscope, the light-source is inserted into the body of the endoscope. Light is emitted from the distal end of the portable endoscope via a light guide arranged in the body of the endoscope when the main switch is turned on and illuminates an object (refer to Japanese Laid-open Patent Publication No. 2003-319906).

SUMMARY OF THE INVENTION

However, in the conventional structure, if the main switch is left on even after the light-source unit is detached from the body of the portable endoscope, the light source continues emitting light, thus wasting the battery. In particular, if the main switch is left on when storing the portable endoscope after use, the battery will be depleted.

Therefore, an object of the present invention is to provide a light-source driver that securely prevents the light source from being left on when the light-source unit is detached from the endoscope body thereby saves electric energy. Furthermore, another aspect of the present invention is to provide a portable endoscope using the above-mentioned light-source driver.

According to the present invention, a light-source driver for a light-source unit detachable from the endoscope body of a portable endoscope is provided.

The light-source driver includes a first switch, a pilot lamp, a warning lamp, a second switch, and a light-switching block.

The first switch switches its status between an On-state and an Off-state in connection with the attachment and detachment of the light-source unit to the endoscope body. The pilot lamp indicates that the illumination light source is being energized. The warning lamp indicates that the output voltage of the battery has dropped to or below a predetermined value. The second switch switches the status of the warning lamp between the On-state and the Off-state in connection with the On-state and the Off-state of the first switch. The light-switching block switches the pilot lamp to the Off-state and further enables the second switch when the second switch is set to the On-state and the output voltage has declined to or below the predetermined value. The second switch is set to the Off-state when the light-source unit is detached from the endoscope body.

Furthermore, according to another aspect of the present invention, a portable endoscope is provided that includes the above-mentioned light-source driver.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
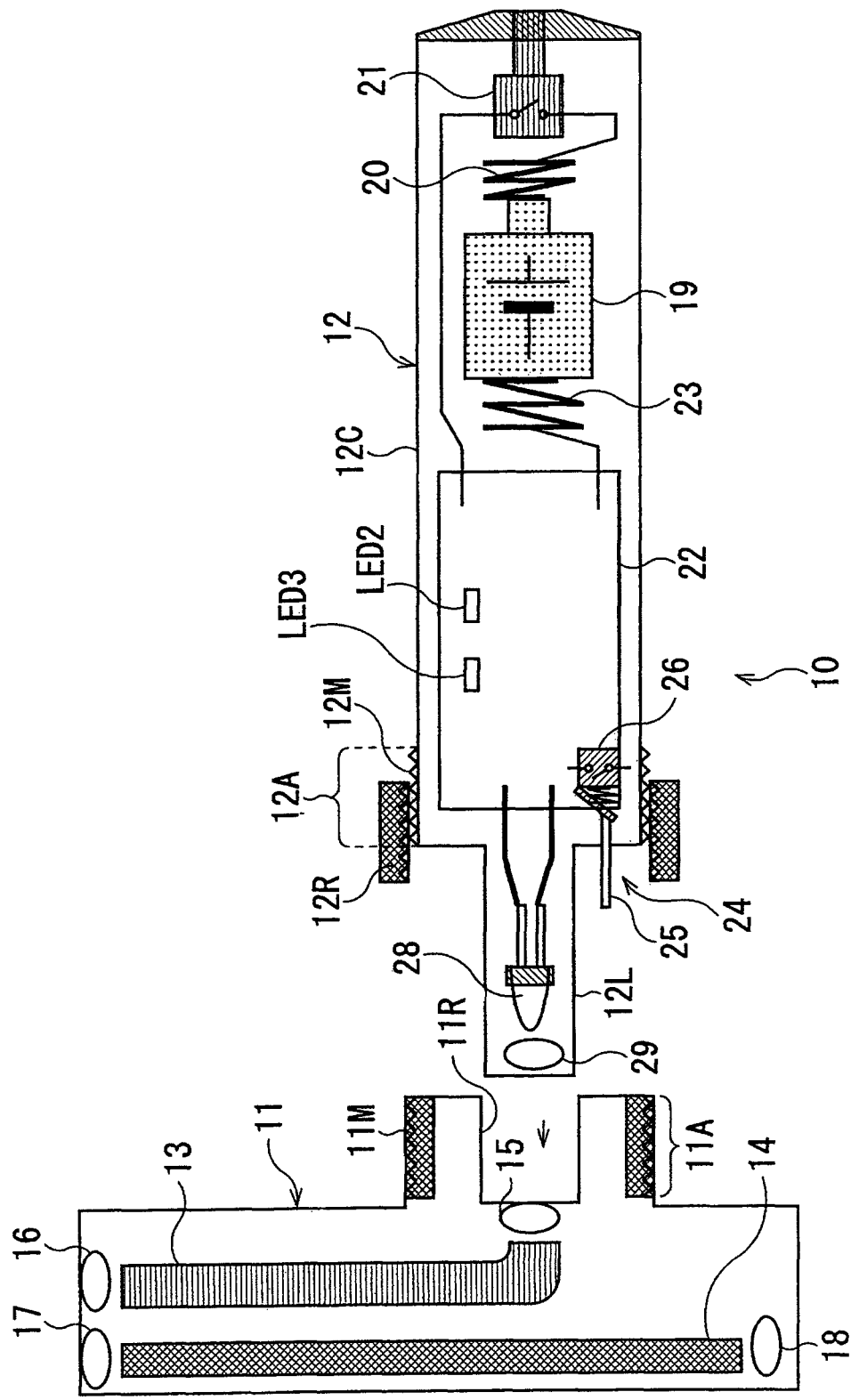
FIG. 1 is a block diagram that schematically illustrates the structure of an embodiment of the portable endoscope to which the present invention is applied.

The present invention is described below with reference to the embodiments shown in the drawings.

FIG. 1 is a block diagram that schematically illustrates the structure of an embodiment of a portable endoscope to which the present invention is applied.

The portable endoscope 10 is comprised of an endoscope body 11 and a light-source unit 12 which is detachable from the endoscope body 11. Inside the endoscope body 11, a light guide 13 and an image guide 14 are arranged. The light guide 13 is for transmitting illumination light to the distal end of the endoscope body 11 and the image guide 14 is for observing an image that is illuminated by the illumination light at the distal end of the endoscope body 11.

One end of the light guide 13, where light is made incident (the incident end face), is disposed at a manipulating portion of the endoscope body 11. A lens 15 is arranged in front of the incident end face. When the light-source unit 12 is attached to the endoscope body 11, light from the light-source unit 12 is concentrated onto the incident end face via the lens 15 and made incident onto the light guide 13. The other end of the light guide 13, where light is emitted (the emitting end face), is disposed at the distal end of an insertion portion of the endoscope body 11. The light incident onto the light guide 13 is transmitted within the light guide 13 and emitted from the emitting end face, and thereby, illuminates a subject through a lens 16.

Furthermore, one end of the image guide 14 is disposed at the distal end of the insertion portion of the endo scope body 11. The illumination light from the light guide 13 is reflected by the subject and made incident onto the image guide 14 through an objective lens 17. The other end of the image guide 14 is disposed at the manipulating portion of the endo scope body 11 and an optical image transmitted via the image guide 14 is observed through an ocular lens 18.

The manipulation portion of the endoscope body 11 is provided with a light-source unit connector 11A for attaching the light-source unit 12. The light-source unit connector 11A has a cylindrical shape and a male thread 11M is provided on the outer surface of the cylinder. At the center of the light-source unit connector 11A, a cylindrical recessed portion 11R is provided coaxially with the light-source unit connector 11A, and the lens 15 is arranged at the bottom of the recessed portion 11R. The recessed portion 11R is a void where a light-source portion 12L of the light-source unit 12 is inserted, as described later.

Inside a casing 12C of the light-source unit 12, a battery(s) 19 is installed. The positive pole of the battery 19 is connected to a light-source drive circuit 30 (see FIG. 2) provided on a light-source circuit board 22 via a main switch 21. The negative pole of the battery 19 is connected to the ground of the light-source drive circuit 30.

The light-source drive circuit 30 is provided with a sensor 24 for detecting attachment of the light-source unit 12 onto the endoscope body 11. An example of the sensor 24 is a push switch that has a pin 25 and a switch 26. The base end of the pin 25 is connected with the switch 26 and the pin 25 is biased toward the tip end direction by a biasing member such as a spring. Namely, the switch 26 is maintained in the Off-state while an external force other than the biasing force from the spring acts on the pin 25. When the tip of the pin 25 is depressed against the biasing force of the biasing member, the pin 25 is pushed inward and thus the switch 26 is switched to the On-state.

A light source for illumination, such as LED 28 (LED1), is provided on the light-source circuit board 22. The light source 28 is driven by the light-source drive circuit 30 provided on the light-source circuit board 22, thus, the lighting of the light source 28 is controlled by the light-source drive circuit 30 and light from the light source 28 is emitted through the illumination lens 29. Furthermore, a green colored pilot lamp LED2 and a yellow colored warning lamp LED3 are also provided on the light-source circuit board 22.

An endoscope connector 12A is provided on the casing 12C of the light-source unit 12. The endoscope connector 12A is a connector half that is connected to the light-source connector 11A when attaching the light-source unit 12 to the endoscope body 11. In this embodiment, the endoscope connector 12A has as a cylindrical shape with the same diameter as the light-source unit connector 11A and the outer surface of connector 12A is provided with a male thread 12M. In addition, a rotational ring member 12R with a female thread on the inner surface is engaged with the male thread 12M.

A cylindrical light-source portion 12L, where the light source 28 and the illumination lens 29 are installed, is provided at the center of the top face of the endoscope connector 12A and extends out along the axis of the cylindrical endoscope connector 12A. Furthermore, the push switch, i.e., sensor 24, is provided on the end face of the endoscope connector 12A which connects the outer periphery of the endoscope connector 12A to the base end of the light-source portion 12L, of which an area is surrounded by the rotational ring member 12R that is engaged with the male thread 12M. Moreover, the sensor 24 (push switch) is arranged such that its axis is parallel with the cylindrical axis of the endoscope connector 12A.

When connecting the light-source unit 12 with the endoscope body 11, the light-source portion 12L is inserted into the recessed portion 11R of the light-source unit connector 11A. The female thread of the rotational ring member 12R is then manually engaged with the male thread 11M of the light-source unit connector 11A. Namely, when the rotational ring member 12R is rotated, the rotational ring member 12R is threaded out from the male thread 12M of the endoscope connector 12A and at the same time engaged with the male thread 11M of the light-source unit connector 11A. Thus, the attachment of the light-source unit 11 to the endoscope body 11 is complete. Note that the endoscope connector 12A is provided with a stop mechanism (not shown) that prevents the rotational ring member 12R from coming out of the endoscope connector 12A.

When the light-source portion 12L of the light-source unit 12 is being inserted into the recessed portion 11R of the light-source unit connector 11A, the tip end of the pin 25 abuts on the top face of the light-source unit connector 11A, which surrounds the recessed portion 11R. Thereby, the pin 25 is pushed into the casing 12 and the switch 26 is turned on. Incidentally, the switch 26 is kept in the Off-state when the light-source unit 12 is disconnected from the endoscope body 11, since no force other than the biasing force of the spring acts on the pin 25.

Figure 2:
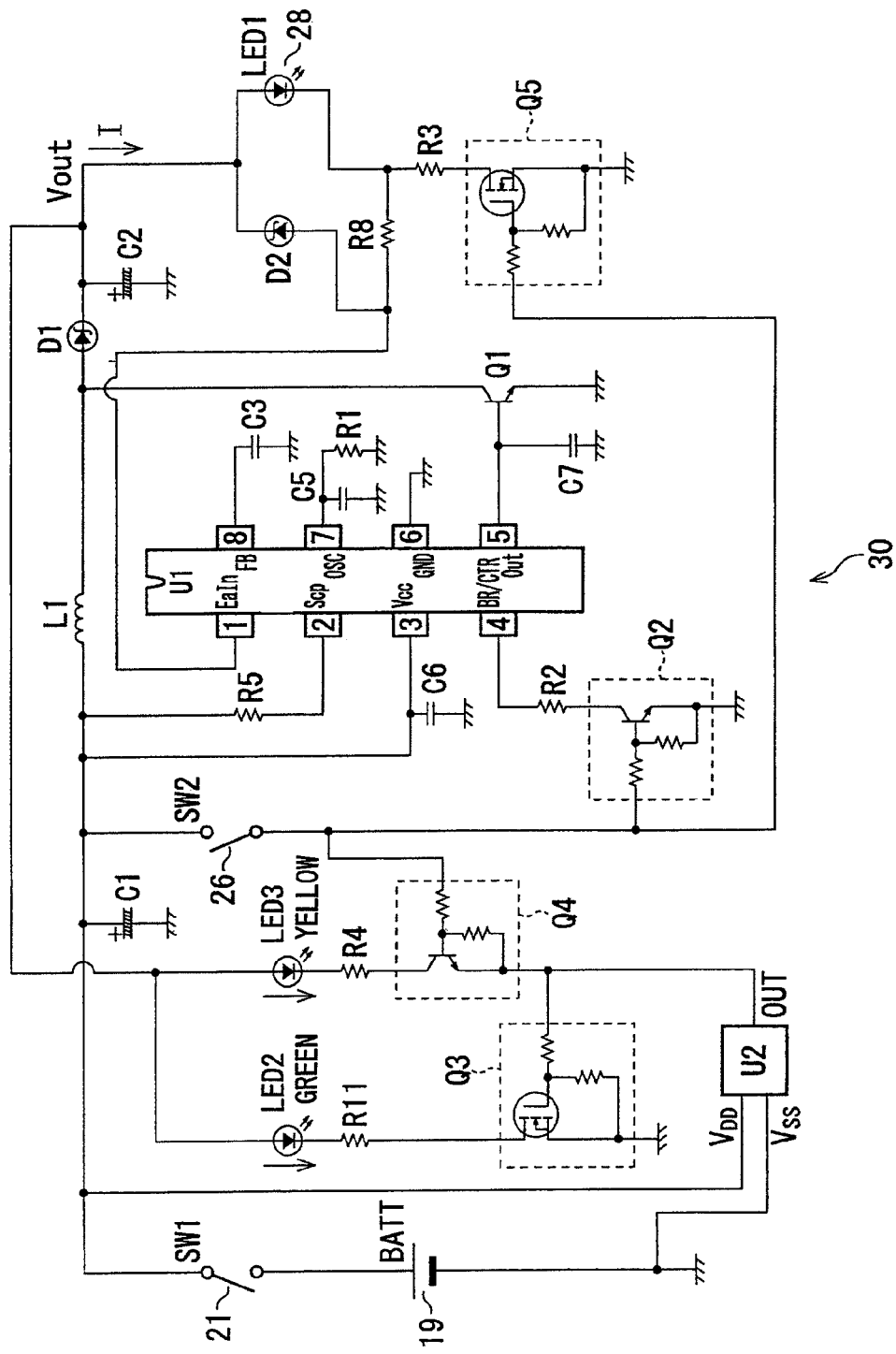
FIG. 2 is a block diagram of a light-source drive circuit of the present embodiment.

With reference to FIG. 2, the structures of the light-source drive circuit 30 of the present embodiment will be explained.

The electric power is supplied from the battery (BATT) 19 through the main switch (SW1) 21 to the light-source drive circuit 30. In the light-source drive circuit 30, a switching regulator U1 is adopted as a step-up DC-DC converter (a step-up controller), so that the voltage of the battery 19 is raised to a predetermined voltage before it is applied to the light source 28.

The switching regulator U1, for example, has the following eight terminals or pins:

Pin #1 (EaIn) is an error amplifier input terminal, at which the application of a voltage controls the pulse-width-modulation (PWM) output from the switching regulator;

Pin #2 (SCP) is a terminal for triggering a soft start and a timer for a short circuit;

Pin #3 (Vcc) is a power supply terminal. An output terminal (pin #5) is fixed at Low when low voltage (e.g., Vcc<1.3V) is input to this terminal in order to prevent an incorrect action of the system;

Pin #4 (BR/CTL) is a break-control terminal for controlling the output current of the output terminal (pin #5) and for setting the ON/OFF state of a standby mode. The standby mode, in which, for example, the power-source current is lower than 1 µA, is set when pin #4 is opened or connected to Vcc;

Pin #5 (Out) is a Totem-Pole type output terminal and connected to an external power transistor Q1;

Pin #6 (GND) is a ground terminal;

Pin #7 (OSC) is a terminal for setting a PWM frequency by connecting a capacitor C5 and a resistor R1 in parallel; and Pin #8 (FB) is an error amplifier output terminal to which a capacitor C3 for phase compensation is connected.

The step-up DC-DC converter is comprised of the switching regulator U1, the power transistor Q1, a coil L1, capacitors C1 and C2, a Schottky diode D1, a switch device Q2, and so on. The positive pole of the battery BATT is connected to the DC-DC converter via the main switch SW1. When the main switch is set to the On-state, current is supplied to the power-supply terminal, such as pin #3, of the switching regulator U1, and in turn, the switching regulator U1 is switched on.

The power transistor Q1 is connected to the output terminal #5 of the switching regulator U1 and the base current is supplied from the output terminal #5. The output of the output terminal #5 is controlled by the input voltage of EaIn terminal #1. The on-duty ratio of the output terminal #5 is set higher when the input voltage of the EaIn terminal #1 drops. Namely, as the input voltage of the EaIn terminal #1 drops, the period in one cycle during which the base voltage of the power transistor Q1 is set to high (i.e., where the power transistor Q1 is set to the On-state) is elongated.

The output terminal of the DC-DC converter is connected to the anode of the LED1 (the light source 28) and the output voltage Vout is applied to the anode of the LED1. The cathode of the LED1 is connected to the ground via a resistor R3 and the switch device Q5, as well as, to the EaIn terminal #1 of the switching regulator U1 through a resistor R8. Namely, the voltage of the cathode of the LED1 is monitored by the EaIn terminal #1 and the power transistor Q1 is driven by a high on-duty ratio when the voltage of the cathode of the LED1 drops.

According to the above structures, the voltage of the battery BATT is raised by the DC-DC converter on the basis of the principle of a step-up converter. Thereby, the switching regulator U1 controls the output voltage Vout such that the current of LED1 is maintained constant.

Furthermore, in the present embodiment, a switch device Q2 is connected to the BR/CTL terminal #4 of the switching regulator U1. An example of the switch device Q2 is a semiconductor device, such as a resistor-built-in transistor which could be a bipolar transistor or an MOS transistor. The BR/CTL terminal #4 is connected to the collector terminal of the switch device Q2 via a resistor R2. The emitter terminal of the switch device Q2 is connected to ground. Furthermore, the base terminal to control the On/Off state of the switch device Q2 is connected to the power-source line via a built-in resistor and the switch SW2 (26), which switches in connection with the attachment of the light-source unit 12 to the endoscope body 11.

Namely, if switch SW2, such as a push switch, is switched on when the main switch SW1 is in the On-state, i.e., when the light-source unit 12 is attached to the endoscope body 11, the switch device Q2 is switched on, and thus the BR/CTL terminal #4 of the switching regulator U1 is connected to ground via the resistor R2. On the other hand, even when the main switch SW1 is on, the switch device Q2 is set to the Off-state when the switch SW2 is switched off and thus the BR/CRT terminal #4 is opened, and in turn, the switching regulator U1 is set to the standby mode.

According to the above-described structures, the LED1 (light source 28) is prevented from being left on even when the light-source unit 12 is detached from the endoscope body 11 while the main switch SW1 is left in the On-state. This is because the switch SW2 of the sensor 24 (push switch) is set to the Off-state when the light-source unit 12 is detached from the endoscope body 11, and thereby the switching regulator U1 is set to the standby mode. Furthermore, the present embodiment has the advantage of reducing the size of the light-source unit 12, since the current that flows in the switch SW2 is reduced thus allowing the use of simpler switch SW2.

Moreover, abnormally high voltage caused by chattering of the switch SW2(26) induced while attaching and detaching the light-source unit 12 to the endoscope body 11 is prevented, and thus the circuit is kept safe, since the switch SW2 is not connected to the coil L1 in series.

Note that a resistor R8 and a Zener diode D2 are provided for protecting from over-voltage when an LED load is opened. Namely, when a feedback loop by the LED1 is opened, a feedback loop via the Zener diode D2 is activated, and thus destruction of the coil L1 and the switching regulator U1 is prevented. In the present embodiment, the description applied to the case of one LED being used, as well as to the case of a plurality of LEDs being used.

The light-source drive circuit 30 of the present embodiment also includes the green pilot lamp LED2 and the yellow warning lamp LED3. The pilot lamp LED2 is lit when the light-source drive circuit 30 is being energized and the warning lamp LED3 is lit when the voltage of the battery BATT drops to a certain level.

The anode of the pilot LED2 is connected to the output terminal (Vout) of the DC-DC converter, and the cathode is connected to ground via a resistor R11 and a switch device Q3. Furthermore, the anode of the warning lamp LED3 is also connected to the output terminal of the DC-DC converter just as the LED2, while the cathode of the warning lamp LED3 is connected to the voltage-detecting circuit device U2 via a resistor R4 and a switch device Q4.

The voltage-detecting circuit device U2 monitors the output voltage of the battery BATT while it also acts as a switch circuit that connects the cathode of the warning LED3 when the output voltage drops to or below a predetermined value. Thereby, the warning lamp LED3 is lit when the remaining electric power of the battery BATT is low and the output voltage decreases.

Both switch device Q3 (which is provided between the resistor R11 connected to the cathode of the pilot lamp LED2 and ground) and the switch device Q4 (which is provided between the resistor R4 connected to the cathode of the warning lamp LED3 and the voltage-detecting circuit device U2) may be semiconductor devices, such as a resistor-built-in transistor which could be a bipolar transistor or an MOS transistor.

The switch device Q4 is a switch for preventing the warning lamp LED3 from being lit when the battery voltage drops to the level at which the warning lamp LED3 is set to light but the DC-DC converter is in the Off-state because the switch SW2 is in Off-state.

Namely, without the switch device Q4, the warning lamp LED3 is lit if the main switch is set to the On-state even when the light-source unit 12 has been detached from the endoscope body 11, i.e., the switch SW2 is Off, and the DC-DC converter is in the Off-state, since the output side of the DC-DC converter is connected to the battery BATT through the coil L1. As for the warning lamp LED3, the lighting is suppressed if it has a high forward voltage drop VF. However, the VF of a color LED is generally low, therefore the switch device Q4 is required.

The switch device Q4 may be a device including a bipolar transistor. The collector terminal of the transistor is connected to a resistor R4 and the emitter terminal is connected to the output terminal (the OUT terminal) of the voltage-detecting circuit device U2. Furthermore, the base terminal is connected to the switch SW2 via a built-in resistor. Thereby, the switch device Q3 is switched on only when the switch SW2 is in the On-state. Therefore, lighting of the warning lamp LED3 while the switch SW2 is in the Off-state is prevented since the warning lamp LED3 is opened when the switch SW2 is in the Off-state.

The switch device Q3 is a switch to turn off the pilot lamp LED2 when the warning lamp LED3 is turned on. Namely, if the warning lamp LED3 is lighted, the lit of the pilot lamp LED2 is not necessary, so that the lamp which is lit switches from the pilot lamp LED2 to the warning lamp LED3 to eliminate unnecessary electric consumption.

The switch device Q3 may be a device including an MOS transistor, and the drain terminal is connected to the resistor R11 and the source terminal is connected to ground. Furthermore, the gate terminal is connected to the emitter terminal of the switch device Q4 via a built-in resistor.

When the battery voltage drops below a predetermined level and the output terminal (OUT terminal) of the voltage-detecting circuit device U2 is set to low (i.e., when the emitter terminal of the switch device Q4 is connected to ground), the gate terminal of the switch device Q3 is set to low and the switch device Q3 is switched to the Off-state. Thus, the pilot lamp LED2 is turned off. At the same time, the cathode of the warning lamp LED3 is connected to ground so that the warning lamp LED3 turns on.

Figure 3:
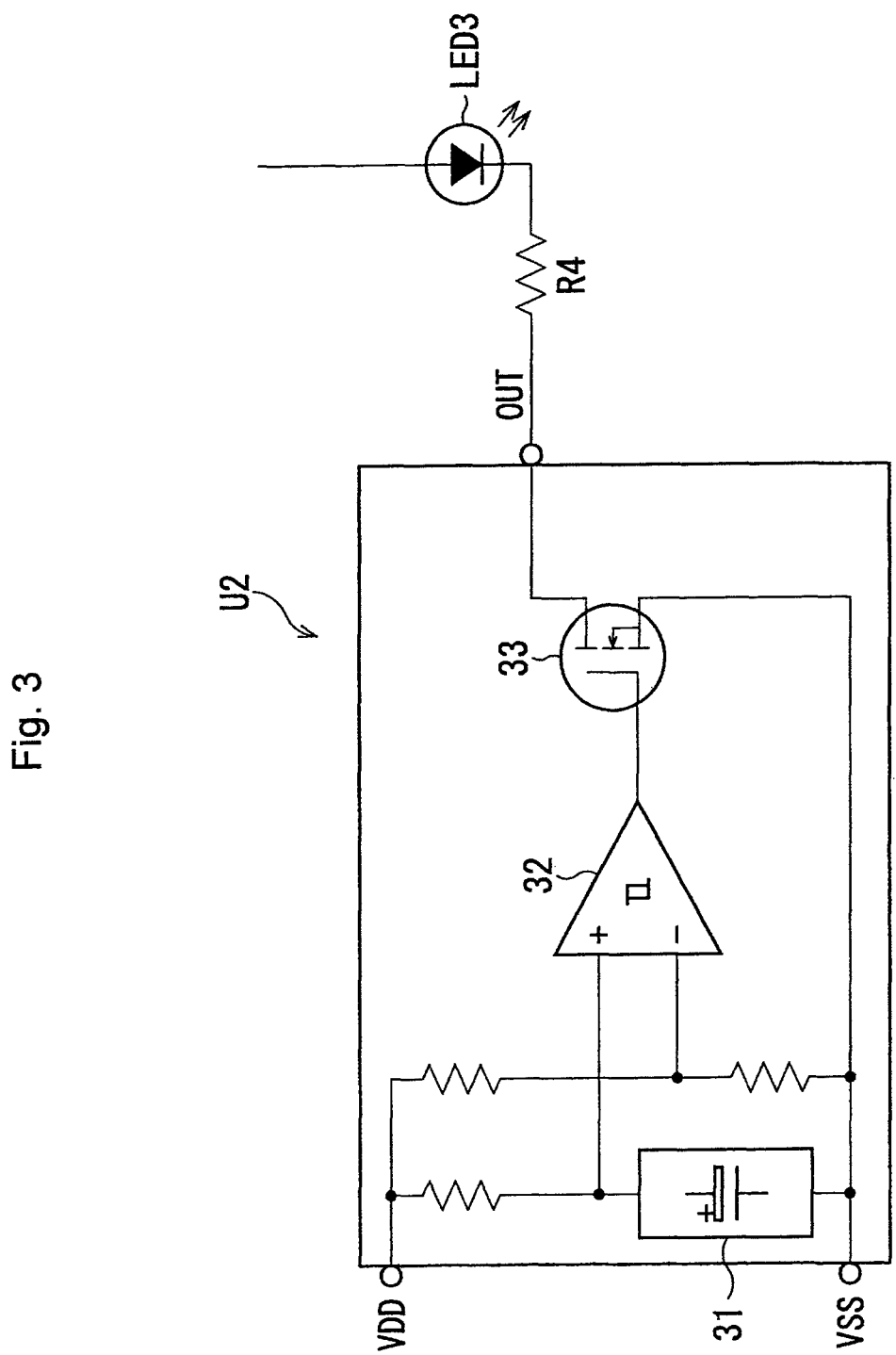
FIG. 3 shows a schematic of a voltage-detecting circuit device.

Operation of the voltage-detecting circuit device U2 will be explained with reference to FIG. 3 which shows a schematic of the voltage detecting circuit device U2. A standard voltage-generating circuit 31 is provided with the voltage-detecting circuit device U2. For example, the standard voltage-generating circuit 31 outputs 2.3 V as a standard voltage. This standard voltage and the voltage ($V_{DD}$-$V_{SS}$) between the positive pole and the negative pole of the battery BATT which is split by the resistance ratio, are input to a comparator 32. The comparator 32 compares the values of the input voltages and determines whether the output voltage of the battery BATT is lower than the standard voltage (here, 2.3 V).

When the voltage in which the split voltage of the battery BATT is lower than the standard voltage, the comparator 32 applies a high voltage to the gate terminal of an N-channel FET 33. Namely, when the output voltage of the battery BATT declines to a level below the predetermined voltage, the split voltage declines to a level lower than the standard voltage, thus the gate terminal of the N-channel FET 33 is set at a high level and current flows between the drain and the source.

Thus, the cathode of the warning lamp LED3 is connected to the ground via the resistor R4 and the switch device Q4 when the switch device Q4 is in the On-state, and in turn, the warning lamp LED3 is lit. Furthermore, at this time, the gate terminal of the switch device Q3 is switched to the low level and the switch device Q3 is switched off, thus turning off the pilot lamp LED2. Namely, the lighting of the LED switches from the pilot lamp LED2 to the warning lamp LED3.

In the present embodiment, a switch device Q5 is provided between ground and the resistor R3, which is used to monitor the current of the illumination LED1. Just as with the switch devices Q2-Q4, the switch device Q5 may be a semiconductor device such as a resistor-built-in transistor which could be a bipolar transistor or an MOS transistor. In the present embodiment, for example, the switch device Q5 is a device including an MOS transistor and its drain terminal is connected to the resistor R3, and the source terminal is connected to ground. Furthermore, the gate terminal is connected to the switch SW2 via a built-in resistor.

The switch device Q5 is a switch to prevent the illumination LED1 from lighting when the light-source unit 12 is detached from the endoscope body 11 despite switch SW2 being in the Off-state and the DC-DC converter being in the Off-state. Namely, if the switch device Q5 is not employed, the illumination LED1 is lit when the main switch SW1 is in the On-state while the battery voltage is maintained at a high level, since the output terminal of the DC-DC converter is connected to the battery BATT through the coil L1.

The lighting of the illumination LED1 during the Off-state of switch SW2 can be prevented if a plurality of LEDs is provided as a multi-level circuit to configure the illumination light-source. However, this increases the number of parts, cost, and heat generation, and reduces the efficiency of the circuit, thus it is not preferable. Therefore, in the present embodiment, the switch device Q5 is provided between ground and the illumination LED1 current-monitoring resistor R3, and the gate terminal is connected to the switch SW2 via the built-in resistor. Thus, when the switch SW2 is in the Off-state, the switch device Q5 is set to the Off-state and the cathode of the illumination LED1 is opened.

Accordingly, when the light-source unit 12 is detached from the endoscope body 11, i.e., when the switch SW2 is in the Off-state, the lighting of the illumination LED1 is securely prevented.

As described above, according to the present embodiment, wasteful lighting of the illumination light source and the warning lamp is prevented when the light-source unit is detached from the endoscope body by implementing this simple configuration. Furthermore, the lighting of the pilot and warning lamps are mutually exclusive, thus electric waste is further prevented.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2006-342152 (filed on Dec. 20, 2006), which is expressly incorporated herein, by reference, in its entirety.

The invention claimed is:

1. A light-source driver of a light-source unit detachable from an endoscope body of a portable endoscope, said light-source driver comprising:
   a first switch that is biased in an Off-state when the light-source unit is detached from the endoscope body, and that switches to an On-state based on attachment of the light-source unit to the endoscope body;
   a pilot lamp which indicates that an illumination light source is being energized;
   a warning lamp which indicates that an output voltage of a battery is dropping to or below a predetermined value;
   a second switch that switches the status of said warning lamp between an On-state and an Off-state in connection with the On-state and the Off-state of said first switch; and
   a light-switcher that switches said pilot lamp to the Off-state and further enables said second switch when said second switch is set to the On-state and the output voltage has dropped to or below the predetermined value;
   wherein said second switch is set to the Off-state when the light-source unit is detached from the endoscope body; and
   wherein one contact of said first switch is connected to a power line and an other contact of said first switch is connected to a terminal that selects the On-state and the Off-state of said second switch.

2. The light-source driver as claimed in claim 1, wherein said light-switcher comprises a further switch, said further switch being connected to said second switch in series and being set to an On-state when the output voltage is less than or equal to the predetermined value.

3. The light-source driver as claimed in claim 2, wherein said light-switcher comprises a third switch, said third switch being connected to said pilot lamp in series and said third switch being set to an Off-state when said further switch is switched to the On-state.

4. The light-source driver as claimed in claim 1, further comprising a main switch that is manually operated.

5. The light-source driver as claimed in claim 1, further comprising a third switch that switches between the On-state and Off-state of the illumination light source and that is connected to the illumination light source in series, wherein a terminal of said third switch that is used to select the On-state and the Off-state of said third switch is connected to said first switch.

6. The light-source driver as claimed in claim 1, further comprising:
   a step-up controller that supplies stepped-up voltage from a power source to the illumination light source, said pilot lamp, and said warning lamp; and
   a fourth switch that is connected to a break-control terminal of said step-up controller for setting a standby mode of said step-up controller;
   wherein an On-state and an Off-state of said fourth switch is controlled by the On-state and the Off-state of said first switch and said step-up controller is set to the standby mode when the light-source is detached from the endoscope body.

7. The light-source driver as claimed in claim 6, wherein the illumination light source is connected to an output terminal of a DC-DC converter including said step-up controller and said step-up controller controls the voltage of said output terminal so as to maintain the electric current of the illumination light source constant.

8. The light-source driver as claimed in claim 7, wherein said pilot lamp is connected to said output terminal of said DC-DC converter including said step-up controller.

9. The light-source driver as claimed in claim 7, wherein said warning lamp is connected to said output terminal of said DC-DC converter including said step-up controller.

10. A portable endo scope comprising a light-source driver of a light-source detachable from an endoscope body of said portable endoscope, the light-source driver comprising:
    a first switch that is biased in an Off-state when the light-source unit is detached from the endoscope body, and that switches to an On-state based on attachment of the light-source unit to the endoscope body;
    a pilot lamp which indicates that the illumination light source is being energized;
    a warning lamp which indicates that the output voltage of a battery has dropped to or below a predetermined value;
    a second switch that switches the status of said warning lamp between an On-state and Off-state in connection with the On-state and the Off-state of said first switch; and
    a light switcher that switches said pilot lamp to an Off-state and further enables said second switch when said second switch is set to the On-state and the output voltage has dropped to or below the predetermined value;
    wherein said second switch is set to the Off-state when the light-source unit is detached from the endoscope body; and
    wherein one contact of said first switch is connected to a power line and an other contact of the first switch is connected to a terminal that selects the On-state and the Off-state of said second switch.

11. The portable endoscope according to claim 10, wherein said light-switcher comprises a further switch, said further switch being connected to said second switch in series and being set to the On-state when the output voltage is less than or equal to the predetermined value.

12. The portable endoscope according to claim 11, wherein said light-switcher comprises a third switch, said third switch being connected to said pilot lamp in series and said third switch being set to an Off-state when said further switch is switched to an On-state.

13. The portable endoscope according to claim 10, further comprising a main switch that is manually operated.

14. The portable endoscope according to claim 10, further comprising a third switch that switches between an On-state and an Off-state of the illumination light source and that is connected to the illumination light source in series, wherein a terminal of said third switch that is used to select the On-state and the Off-state of said third switch is connected to said first switch.

15. The portable endoscope according to claim 10, further comprising:
    a step-up controller that supplies stepped-up voltage from a power source to the illumination light source, said pilot lamp, and said warning lamp; and
    a fourth switch that is connected to a break-control terminal of said step-up controller for setting a standby mode of said step-up controller;
    wherein an On-state and an Off-state of said fourth switch is controlled by the On-state and the Off-state of said first switch and said step-up controller is set to the standby mode when the light-source unit is detached from the endoscope body.

16. The portable endoscope according to claim 15, wherein the illumination light source is connected to an output terminal of a DC-DC converter including said step-up controller and said step-up controller controls the voltage of said output terminal so as to maintain the electric current of the illumination light source constant.

17. The portable endoscope according to claim 16, wherein said pilot lamp is connected to said output terminal of said DC-DC converter including said step-up controller.

18. The portable endoscope according to claim 16, wherein said warning lamp is connected to said output terminal of said DC-DC converter including said step-up controller.

19. The light source driver according to claim 1, said second switch comprising a semiconductor device including a bipolar transistor or a MOS transistor.

20. The portable endoscope according to claim 10, said second switch comprising a semiconductor device including a bipolar transistor or a MOS transistor.

* * * * *